United States Patent
Chavan et al.

(10) Patent No.: US 9,480,864 B2
(45) Date of Patent: Nov. 1, 2016

(54) MARINE BASED COSMETIC ACTIVE INGREDIENTS AND USE THEREOF

(75) Inventors: Manasi Chavan, Stony Brook, NY (US); Yuhua Sun, Stony Brook, NY (US); Christine Williams, Hauppauge, NY (US); Michael Sunkin, Long Beach, CA (US)

(73) Assignee: BASF Corporation

( * ) Notice: Subject to any disclaimer, the term of this patent is extended or adjusted under 35 U.S.C. 154(b) by 220 days.

(21) Appl. No.: 13/588,210

(22) Filed: Aug. 17, 2012

(65) Prior Publication Data

US 2013/0045197 A1 Feb. 21, 2013

Related U.S. Application Data

(60) Provisional application No. 61/524,698, filed on Aug. 17, 2011.

(51) Int. Cl.
| | | |
|---|---|---|
| *A61K 8/97* | (2006.01) | |
| *A61Q 19/08* | (2006.01) | |
| *C12P 1/02* | (2006.01) | |
| *C12N 1/12* | (2006.01) | |
| *C12N 1/16* | (2006.01) | |
| *C12N 1/18* | (2006.01) | |

(52) U.S. Cl.
CPC ............... *A61Q 19/08* (2013.01); *C12N 1/12* (2013.01); *C12N 1/16* (2013.01); *C12N 1/18* (2013.01); *C12P 1/02* (2013.01); *A61K 8/975* (2013.01)

(58) Field of Classification Search
CPC .............................. A61Q 19/08; A61K 8/97
USPC ............................................. 424/115; 435/171
See application file for complete search history.

(56) References Cited

U.S. PATENT DOCUMENTS

| | | | |
|---|---|---|---|
| 4,459,285 A * | 7/1984 | Grollier et al. ................. | 424/74 |
| 5,508,033 A | 4/1996 | Briand | |
| 6,416,769 B1 | 7/2002 | Vromen | |
| 7,090,875 B2 | 8/2006 | Miyazaki et al. | |
| 7,220,417 B2 * | 5/2007 | Nizard .................... | A61K 8/975 424/195.17 |
| 2003/0219456 A1* | 11/2003 | Ok ........................... | C12N 1/18 424/195.16 |
| 2004/0029829 A1 | 2/2004 | Miyazak et al. | |
| 2004/0108608 A1 | 6/2004 | Ju et al. | |
| 2006/0269494 A1 | 11/2006 | Gupta | |
| 2007/0004647 A1 | 1/2007 | Arbiser | |
| 2007/0172492 A1 | 7/2007 | Soma et al. | |
| 2008/0226740 A1 | 9/2008 | Chen et al. | |
| 2009/0130139 A1 | 5/2009 | Mekideche | |
| 2010/0047219 A1 | 2/2010 | Ceccoli et al. | |
| 2011/0002969 A1 | 1/2011 | Serraima et al. | |

FOREIGN PATENT DOCUMENTS

| | | | | |
|---|---|---|---|---|
| CN | 101528194 A | 9/2009 | | |
| IT | EP 1228752 A2 * | 8/2002 | ............... | A61K 8/02 |
| JP | 61-087614 A | 5/1986 | | |
| JP | 2006104117 A2 | 4/2006 | | |
| JP | 2006104118 A2 | 4/2006 | | |
| WO | WO-2008/039515 A2 | 4/2008 | | |
| WO | WO 2010042842 A2 * | 4/2010 | | |

OTHER PUBLICATIONS

Liu et al., Experimental and Molecular Medicine, vol. 43, No. 9, p. 487-493, 2011.*
Santos, A Manual for the Processing of Agar From Gracilaria, ASEAN/SF/90/Manual No. 5, p. 1-37, 1990.*
Byoung Chan Kim et al., "Highly stable trypsin-aggregate coatings on polymer nanofibers for repeated protein digestion", Proteomics; 9(7) pp. 1893-1900; Apr. 2009.
Office Action from corresponding Chinese Patent Application No. 201180014449.8 dated Jul. 16, 2013 (English translation attached).
International Search Report on Patentability Feb. 26, 2013.
English Language Abst. of JP 61-87614 May 6, 1986.
Kursar et al., "Light harvesting system of the red alga *Gracilaria tikvahiae*. Biochemical analyses of pigment mutations", Plant Physiology, vol. 73, No. 2, pp. 353-360 (1983).
Cote et al., "Production and Properties of Native Agars from *Gracilaria tikvahiae* and other Red Algae", Botanica Marina, vol. 29, pp. 359-366 (1986).
Xie, M.Y. et al. Practical Production Technolgy and Formulation for Daily Chemicals 1st ed, Jiangxi Science and Technology Press, published on Jun. 30, 2002, lines 20-23 on p. 72.
Prachyakij et al., "Improvement in the quality of a fermented seaweed beverage using an anti-yeast starter of *Lactobacillus plantarum* DW3 and partial sterilization", Wolrd Journal of Microbiology and Biotechnology, vol. 24. No. 9, pp. 1713-1720 (Jan. 19, 2008).

* cited by examiner

*Primary Examiner* — Chris R Tate
*Assistant Examiner* — Douglas F White
(74) *Attorney, Agent, or Firm* — Drinker Biddle & Reath LLP

(57) ABSTRACT

The present invention relates to a cosmetic and/or pharmaceutical active component for stimulating proteasome activity of skin cells comprising the broth obtained by inoculating a biomass of the algae, *Gracilaria* spp., particularly the algae, *Gracilaria tikvahiae*, with a yeast culture, and allowing fermentation of the biomass to produce a fermentation broth. Also described is a cosmetic and/or pharmaceutical active component for stimulating proteasome activity of skin cells comprising an extract of the algae, *Gracilaria tikvahiae*. The present invention also relates to topical compositions comprising as a cosmetic and/or pharmaceutical active component a ferment of the algae, *Gracilaria* spp., particularly the algae, *Gracilaria tikvahiae*, or an extract of the algae, *Gracilaria tikvahiae*, or a combination of both.

17 Claims, 8 Drawing Sheets

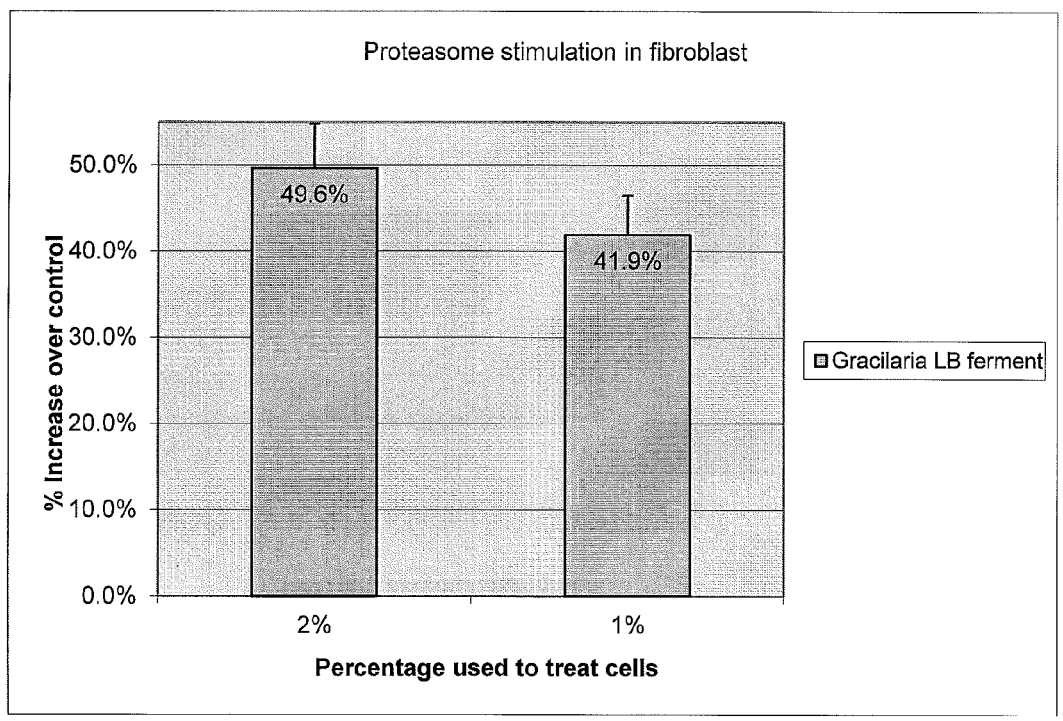
FIG. I

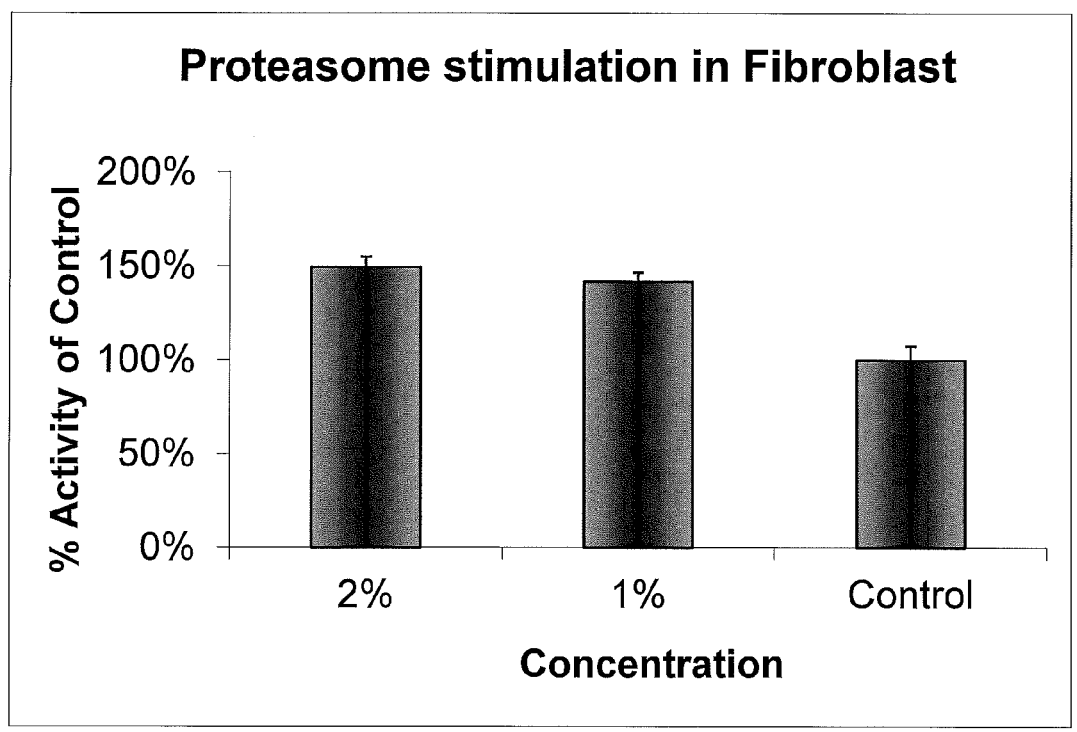
FIG. II

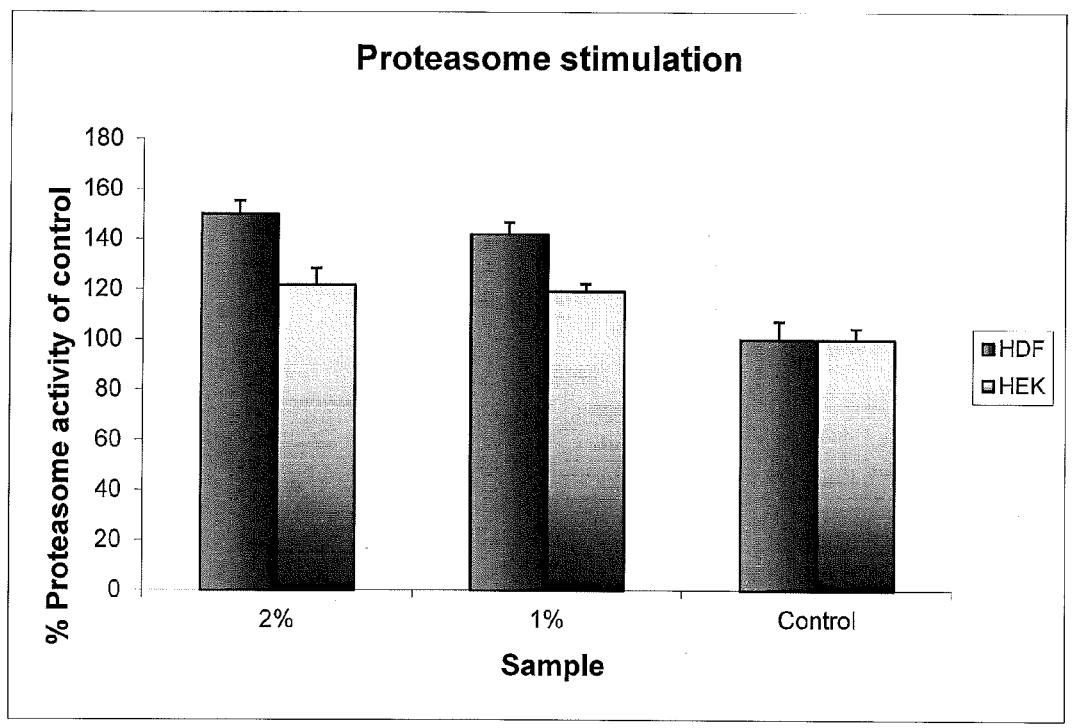
FIG. III

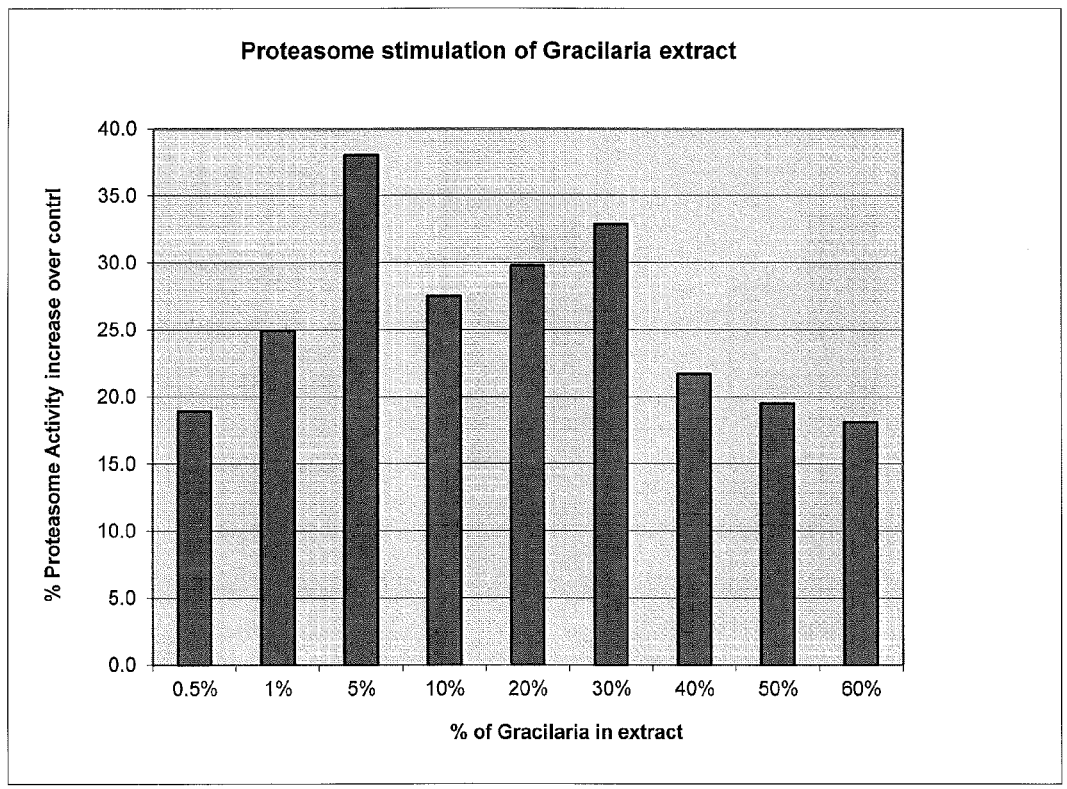
FIG. IV

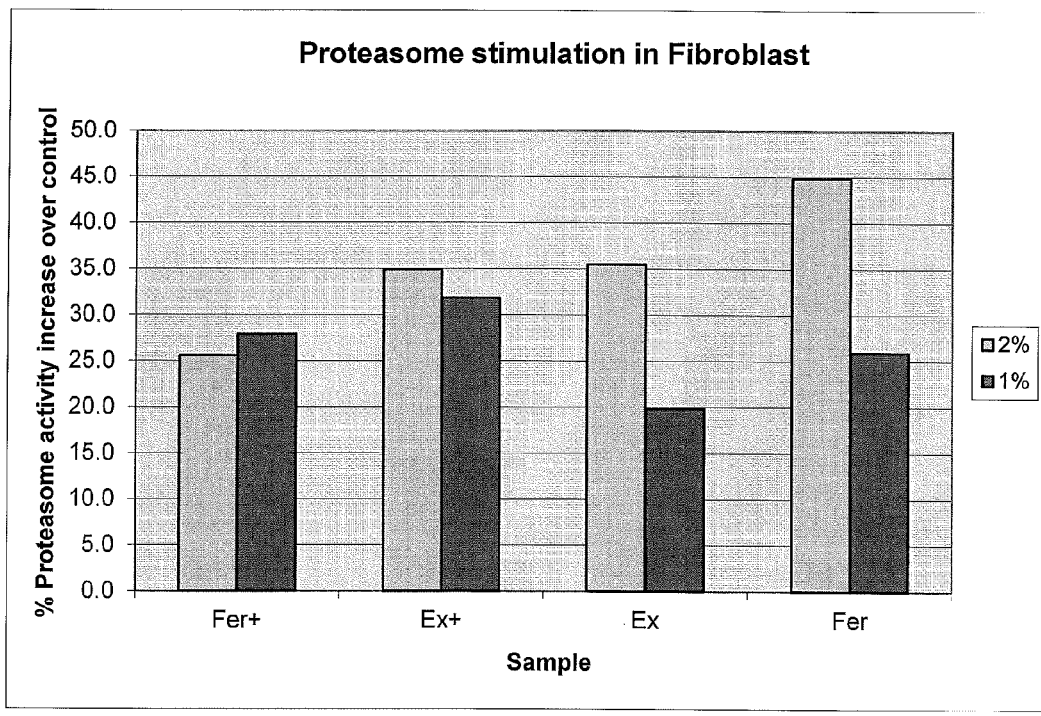
FIG. V

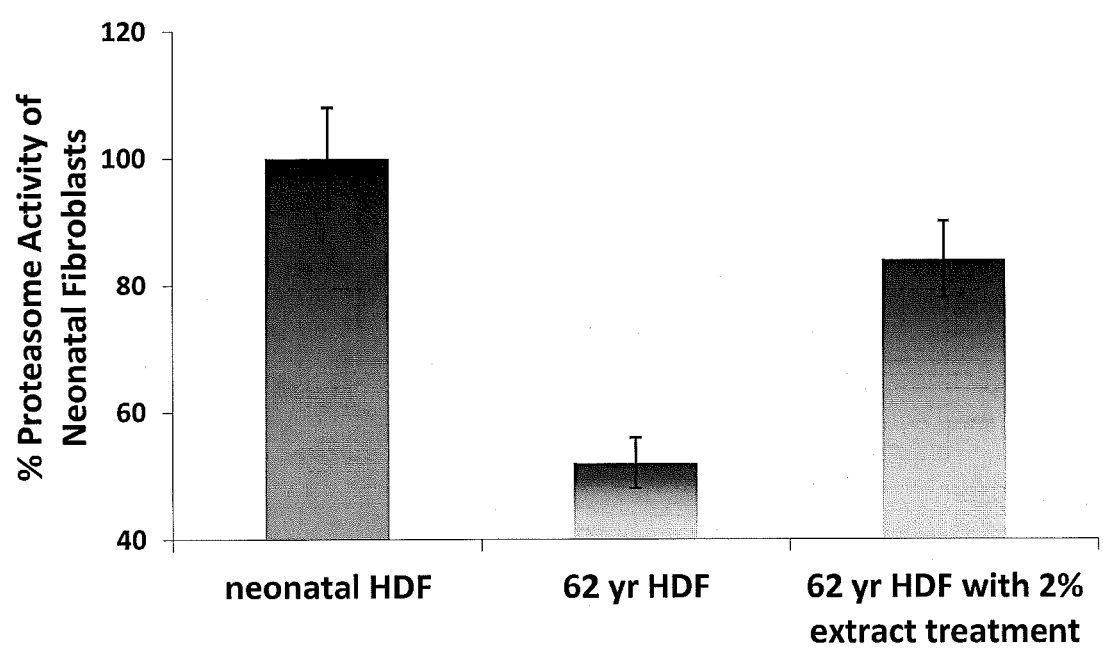
FIG. VI

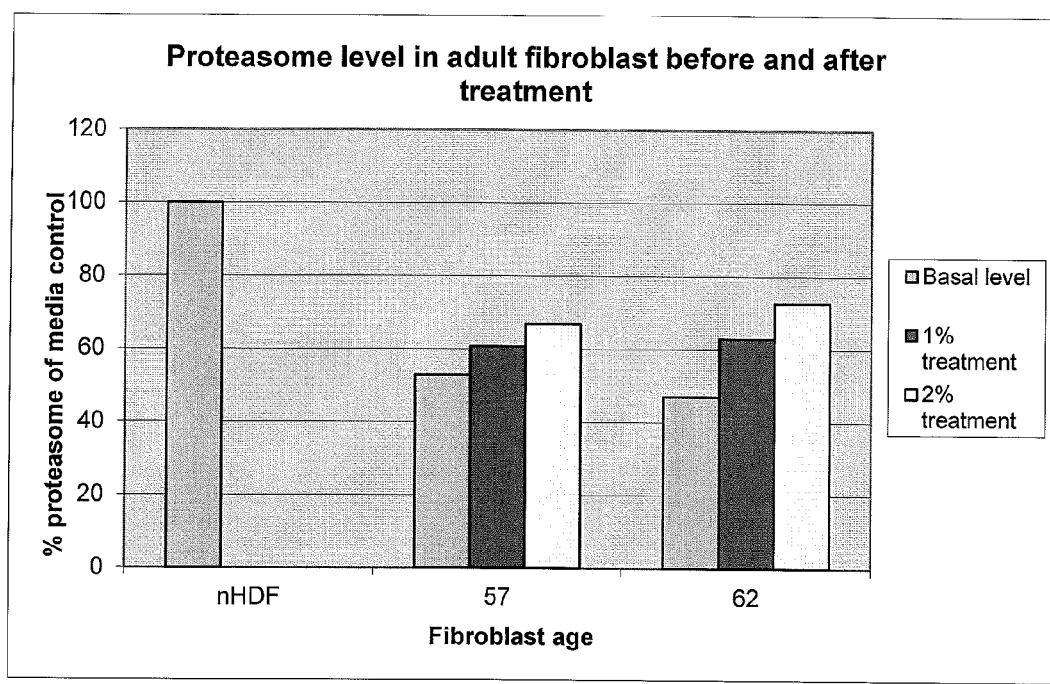
FIG. VII

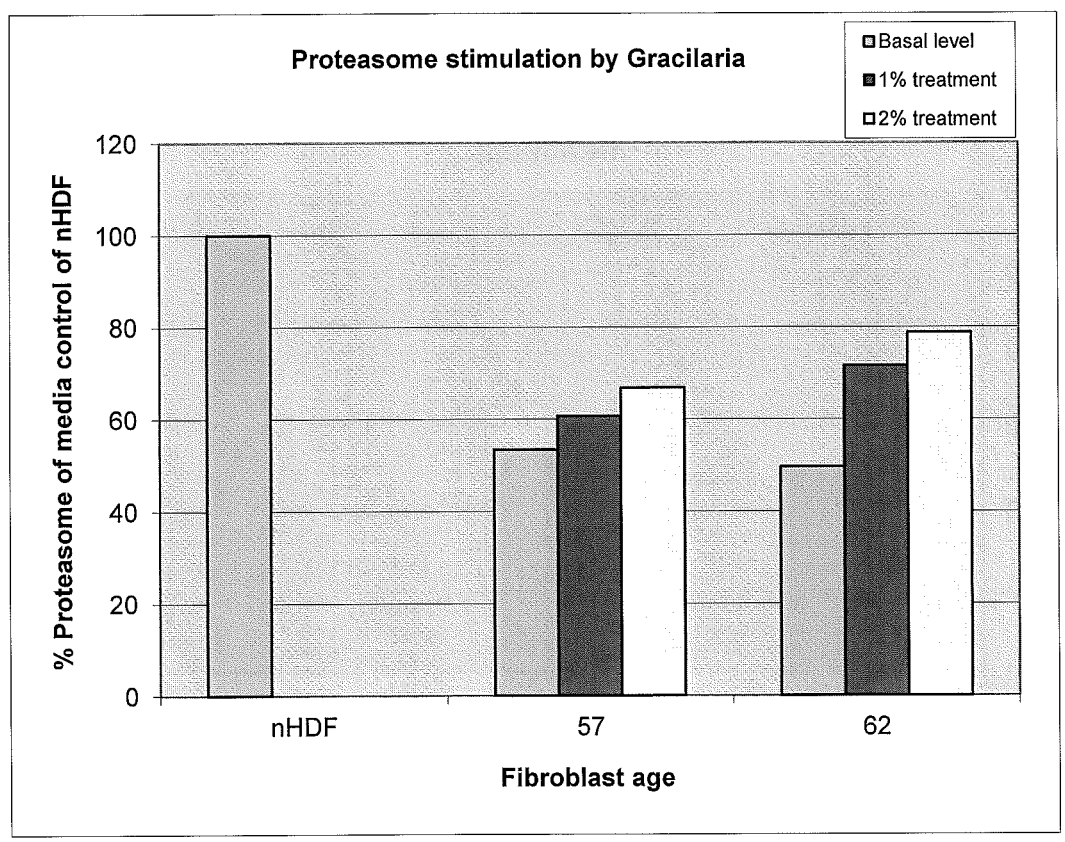
FIG. VIII

MARINE BASED COSMETIC ACTIVE INGREDIENTS AND USE THEREOF

CROSS REFERENCE TO RELATED APPLICATIONS

The present application claims priority from U.S. provisional patent Ser. No. 61/524,698, filed Aug. 17, 2011.

FIELD OF THE INVENTION

The present invention relates to a cosmetic and/or pharmaceutical and/or personal care active component for stimulating the proteasome activity of skin cells comprising the broth obtained by inoculating a biomass of the algae, *Gracilaria* spp., particularly the species, *Gracilaria tikvahiae*, with a live yeast culture, and allowing fermentation of the biomass to produce a fermentation broth. The present invention also relates to a cosmetic and/or pharmaceutical and/or personal care component for stimulating proteasome activity of skin cells comprising an extract of *Gracilaria tikvahiae*.

The present invention also relates to topical compositions comprising as cosmetic and/or pharmaceutical active component a ferment of the algae, *Gracilaria* spp., particularly the algae, *Gracilaria tikvahiae*, and/or an extract of the algae, *Gracilaria tikvahiae*.

BACKGROUND OF THE INVENTION

Proteasomes are large protein complexes inside all eukaryotes and archaea, as well as in some bacteria. In eukaryotes, proteasomes are located in the nucleus and the cytoplasm of cells. They are the machinery in the cells that degrade and recycle unneeded or damaged proteins into their component amino acids through proteolysis, a chemical reaction which breaks peptide bonds. In this manner, proteasomes help cells regulate the concentration of particular proteins and eliminate proteins which are oxidized, misfolded or have otherwise been damaged. Enzymes that carry out these reactions are called proteases.

It is well known in the cosmetic field that the levels of proteasome activity in skin decline during the aging process, whether chronological aging or accelerated aging due to extrinsic factors such as UV radiation, smoking or pollution. In part, the reduction in proteasome activity results in the accumulation of oxidized and other damaged proteins within the skin cells, and produces an undesirable effect on the appearance of the skin, in particular a "dull" or "uneven" appearance. Thus, it is desirable to increase the levels of proteasome in aged skin for an anti-aging, detoxifying and/or radiance enhancing effect on such skin. Increasingly, however, consumers desire such effects to be achieved through products which have a perceived "natural" origin and there is a continuing need to formulate cosmetic products with ingredients based on plants and the like.

Marine plants, such as algae, have developed mechanisms and chemistries to protect and defend against the extreme environmental conditions which may be found in the ocean, such as, for example, desiccation (high salt), solar radiation and high pressure, and have adapted to become capable of surviving in diverse marine environments. Many algae have historically been and continue to be utilized for health and beauty as part of medicinal remedies, daily diets or dietary supplements, or cosmetics.

It has been discovered that extracts of *Gracilaria tikvahiae*, stimulate the proteasome activity of skin cells when applied to the skin. It has been further discovered that ferments of algae of the genus, *Gracilaria*, particularly ferments of the species, *Gracilaria tikvahiae*, stimulate the proteasome activity of skin cells when applied topically. Thus, through the application of topical cosmetic, pharmaceutical, or personal care compositions comprising the ferments and/or extracts of the present invention, it is possible to increase proteasome activity in chronologically or extrinsically aged skin and/or proactively maintain proteasome activity in skin.

Thus, the present invention relates to marine extracts and fermentations of the genus *Gracilaria*, such as, for example, the species, *Gracilaria tikvahiae*, for use in cosmetic compositions to improve the condition of the skin and/or to provide anti-aging effects.

The present invention further relates to the topical use of the described marine extracts and fermentations to stimulate proteasome activity in skin cells.

The present invention also relates to cosmetic compositions, such as gels, lotions or creams, comprising safe and effective amounts of the marine extracts and/or fermentations of the present invention, alone or in combination with other skin care actives having beneficial anti-aging or other skin enhancing effects.

These and other features and advantages of the present invention will become evident to those skilled in the art from a reading of the present disclosure.

BRIEF DESCRIPTION OF THE DRAWINGS

FIG. 1 is a graph showing the percent increase of proteasome stimulation in fibroblasts over the control for a *Gracilaria tikivahiae* ferment at 2% and 1%.

FIG. 2 is a comparative graph showing the percent activity of control for proteasome stimulation in fibroblast cells for a *Gracilaria tikivahiae* ferment at 2% and 1% and the control.

FIG. 3 is a further graph showing the percent of proteasome stimulation over control for a a *Gracilaria tikivahiae* ferment at 2% and 1% and the control.

FIG. 4 is a graph showing the percent increase of proteasome stimulation of fibroblasts, over the control, for *Gracilaria tikivahiae* extracts, wherein the extracts were 0.5%, 1%, 5%, 10%, 20%, 30%, 40%, 50%, and 60% *G. tikvahiae* by weight.

FIG. 5 is a comparative graph showing the percent increase of proteasome stimulation in fibroblasts over the control for ferments and/or extracts and/or combinations thereof (as indicated in the Table).

FIG. 6 is a graph comparing the proteasome activity of neonatal human dermal fibroblasts to the proteasome activity of aged 62 years human dermal fibroblasts before and after treatment with a *Gracilaria tikivahiae* ferment.

FIG. 7 is a graph comparing the proteasome level in adult aged (aged 57 years and aged 62 years) human dermal fibroblast to neonatal human dermal fibroblasts after treatment with *Gracilaria tikivahiae* ferments.

FIG. 8 is a graph comparing the proteasome stimulation in adult aged (aged 57 years and aged 62 years) human dermal fibroblast to neonatal human dermal fibroblasts after treatment with *G. tikvahiae* ferments.

DETAILED DESCRIPTION

All percentages and ratios used herein are by weight of the total composition unless otherwise designate, and all temperatures are in degrees Celsius unless otherwise designated.

The term "safe and effective" amount as used herein means an amount of a compound or composition sufficient to induce a positive benefit as described herein, but low enough to avoid any serious side effects in the judgment of the skilled artisan.

As used herein, improving the condition of the skin includes diminishing, minimizing and/or preventing irregularities of the skin which can be detected visually or by feel, such irregularities including but not limited to, wrinkles, unevenness or roughness, loss of skin elasticity, sagging, loss of skin recoil from deformation, and sallowness.

It has been surprisingly found that the extractions and fermentations of the marine algae, *Gracilaria* spp., preferably of *Gracilaria tikvahiae*, have a beneficial effect on the condition of the skin when applied topically. More particularly, such extractions and fermentations stimulate the proteasome activity in the skin cells.

*Gracilaria* is a genus of red macroalgae, often sold under the Hawaiian common name "ogo", although it is important to note the common name "ogo" may also be used in the context of other genus of red macroalgae. *Gracilaria* includes the following species: *G. tikvahiae* (synonym: *G. foliifera* var. *angustissima*), *G. gracilis* (synonym *G. verrucosa*), *G. parvispora*, *G. vermiculophylia* (synonym: *G. asiatica*).

Wild *Gracilaria*, and particularly *G. tikvahiae* is widely distributed throughout the world and can be found in the cold temperate regions along the eastern Atlantic coast to warm, subtropical regions in the Caribbean and around the Gulf of Mexico as far south as Colombia and Venezuela. It is also grown via aquaculture techniques in the Hawaiian Islands and other locations. Often associated with eutrophic conditions, it is able to tolerate large environmental variations in the levels of nitrogen, irradiance and temperature.

The species, *G. tikvahiae*, grows free or attached to rocks, particularly limestone and basalt substrates, in intertidal zones such as estuaries and bays. It can reach a height of 30 cm (Littler and Littler 1989). The productivity of this species can be as high as any terrestrial crop on earth. Optimal growth occurs between 24° C. and 30° C. (Hanisak in Hwang, Williams and Brinkhuis 1987), and it has been shown to survive, but not grow, at temperatures below 12° C. (LaPointe and Ryther 1981).

The *Gracilaria* spp. of the present invention may be naturally occurring (e.g, "wild") or cultivated. In one example embodiment, algae of the species, *Gracilaria tikvahiae*, is utilized in the present invention which has been aquacultured on land in pond/raceways in Hawaii using natural seawater from deep ocean sources. *Gracilaria* spp. suitable for use may be obtained from commercially available sources, such as Poisidean Ocean Sciences of New York, N.Y., USA), and Royal Hawaiian Sea Farms (Hawaii, USA).

Other *Gracilaria* species are available from commercial sources known to those skilled in the art. For example, *G. verrucosa* is sold by Radiant, Inc. (South Korea). *G. vermiculophylia* is sold by Koei Kogyo KK (Japan). Both *G. verrucosa* and *G. Vermiculophylia* are in the PCPC ingredient database.

For use in industrial cosmetic applications, it may be preferred to use cultivated algae since cultivation reduces the risk that supplies of the algae will become limited as marine environmental conditions change over time and/or as the aquaculture industry expands. Such cultivated algae may include those produced through a hydroponic-type of cultivation wherein the growth environment may be carefully controlled and the resulting harvests may have a more consistent quality which is highly desirable for industrial applications such as cosmetics.

The alga may be raw, fresh biomass or may be frozen by methods known to one skilled in the art. In one exemplary method, the freezing is affected on raw, fresh biomass at a temperature of between −40° C. and −20° C. for a period of between 1 and 7 days.

An extract of the alga, *Gracilaria tikvahiae*, may be obtained by extraction methods known to those skilled in the art. The extraction may be obtained by aqueous extraction or extraction with an alcohol or a water/alcohol mixture, wherein said alcohol may be isopropanol, ethanol and methanol Preferably, the extract is an aqueous extraction from raw or frozen whole plants. The amount of alga utilized in any given extraction process will vary based on the methodology used and the cost, but preferably may comprise between about 0.5% algae to about 60% algae.

A ferment of the alga *Gracilaria* spp. is obtained by inoculating a biomass of algae of the species *Gracilaria* with a live yeast culture and allowing fermentation of the biomass to produce a fermentation broth. The terms "fermentation broth", "fermentation liquor", "fermentation extract" or "ferment" is used interchangeably herein and mean the media resulting from algae or plant derived material that has been subjected to one or more fermentation stages. In one example embodiment, the ferment is of the species, *Gracilaria tikvahiae*. The live yeast culture may be comprised of *Saccharomyces cerevisae* or *Zygosaccharomyces rouxii* in an appropriate nutrient broth. *Saccharomyces cerevisae* is a species of budding yeast. It is the microorganism behind the most common types of fermentations and is commonly known as "baker's yeast". *Zygosaccharomyces rouxii* is a yeast commonly known from winemaking technology. In the manufacture of wine, it is often a "secondary fermenter", e.g., an incidental organism as opposed to one intentionally added to the grapes. The time and temperature of the fermentation process utilized for the present invention may be determined by one skilled in the art based on the species of yeast and includes, for example, the process described in published U.S. patent application no. 20050089499. The fermentation liquor may further be subjected to pasteurization, sterilization, purification, filtration, concentration, or combinations thereof.

In one embodiment, a biomass of *Gracilaria* spp., such as, for example, raw, fresh *G. tikvahiae* or fresh-frozen *G. tikvahiae*, is mixed at 10% w/w with a yeast, such as, for example, *Z. rouxii*, and allowed to ferment for 2 to 4 days at a temperature range between about 30° C. to about 35° C.

As specified previously, the extracts and ferments of the present invention are particularly useful as active ingredients in cosmetic compositions. These cosmetic compositions can be processed in a conventional manner by one skilled in the art and are particularly suitable for application to wrinkled, lined, rough, aged, and/or UV-damaged skin to improve the appearance thereof as well as for application to healthy and/or young or aging skin to prevent or retard deterioration of the skin, particularly the reduction of proteasome activity.

A method of cosmetic skin care is also disclosed, comprising the topical application to the skin of a person in need thereof, a safe and effective amount of a ferment or extract of the algae, *Gracilaria* spp., particularly *Gracilaria tikvahiae*, in order to obtain a preventive or restorative effect on the skin.

The upper and lower limits for the quantity of an extract or fermentation according to present invention in any given cosmetic formulation is based on the desired effect of the cosmetic composition, the other components of the formulation, the type of composition, cost and manufacturing practicality. However, the extract or ferment of the present invention may be included in a quantity between about 0.1% and about 5%, based on the final weight, preferably between about 1% and 3%.

Topical compositions, for example, cosmetic formulations, comprising the *Gracilaria* spp. extracts or ferments of the present invention may further comprise other topically acceptable ingredients known to those skilled in the art, such as, for example, at least one ingredient selected from the group consisting of preservatives, emollients, emulsifying agents, surfactants, moisturizers, gelling agents, thickening agents, conditioning agents, film-forming agents, stabilizing agents, anti-oxidants, texturizing agents, gloss agents, mattifying agents, solubilizers, pigments, dyes, and fragrances. The term "topically acceptable", as used herein, means the ingredient is suitable for contact with human skin, including the scalp, without undue toxicity, incompatibility, irritation, instability, allergic response, and the like.

Advantageously, the compositions cited above are formulated into a form selected from the group consisting of a solution, aqueous or oily, a cream or an aqueous or oily gel, in particular in a pot or a tube, a shower gel, a shampoo; a milk; an emulsion, a microemulsion or a nanoemulsion, especially oil-in-water or water-in-oil or multiple or siliconized; a lotion, in particular in a glass or plastic bottle or dispensing bottle or aerosol; an ampoule; a liquid soap; a dermatological cake; a ointment; a foam; an anhydrous product, preferably liquid, paste or solid, for example in the form of a stick; and powders.

In one embodiment, the cosmetic composition of the invention is in the form of an anti-wrinkle or anti-aging cream, in particular intended to be applied on skin termed "aged" (e.g, skin from an individual having a chronological age of 40 or more years), a composition for sensitive and/or irritated skin, or a product for making up the skin of the face, body or lips such as a foundation or a lipstick. In one advantageous embodiment, the cosmetic composition of the invention is a composition protecting skin against UV damages, notably a sunscreen composition and/or an after-sun care composition.

The *Gracilaria* spp. extracts or *Gracilaria*/yeast ferments may be used as the sole active component in a cosmetic formulation, or in combination with one or more active components. Advantageous topical cosmetic or pharmaceutical compositions may comprise one or more *Gracilaria* spp. extracts or ferments and one or more proteases selected from the group papain, ficin, bromelain, and actinidin. In one example embodiment, the proteases are stabilized proteases, and more preferably, one or more proteases may be stablized proteases formed by crosslinking such as those described in US 2011-0177052 (Chavan), incorporated herein by reference. Further advantageous topical cosmetic or pharmaceutical compositions comprise one or more *Gracilaria* spp. extracts or ferments and one or more additional skin care ingredients capable of stimulating, improving or otherwise regulating proteasome activity in the skin, such as, by way of example, those described in US 2009-0130139 (Mekideche), U.S. Pat. No. 7,220,417 (Nizard et al), and U.S. Pat. No. 7,919,468 (Reboud-Ravaux, et al), all of which are incorporated herein by reference.

Additional preferred topical cosmetic or pharmaceutical compositions may comprise one or more additional marine-derived topical skin care ingredients having similar, additional, and/or complementary beneficial skin effects. By way of example, suitable additional marine-derived topical skin care ingredients for use in such topical compositions may include those described in US 2010-0047219 (Ceccoli et al), US 2010-0316720 (Statz et al), US 2009-0142370 (Shih et al), U.S. Pat. No. 7,128,914 (Leclerc et al), U.S. Pat. No. 7,220,517 (Nizard et al), all of which are incorporated herein by reference, and *Chondrus crispus* extract.

Many other cosmetically active ingredients are known to a person skilled in the art for improving the health and/or physical appearance of the skin. The skilled person will know how to formulate the cosmetic or dermatological compositions in order to obtain the desired overall benefits intended to be conferred by the composition as well as the desired characteristics of the formulation itself (i.e., small, color, feel). The CTFA Cosmetic Ingredient Handbook, Second Edition (1992) describes various cosmetic and pharmaceutical active and inactive ingredients which are routinely used in the cosmetics and pharmaceuticals industry which are suitable for topical use and may be used in combination with the marine extracts and ferments of the present invention. Non-limiting examples of these classes of ingredients include the following compounds: abrasives, absorbants, compounds with an aesthetic aim such as fragrances, pigments, dyes, essential oils, astringents, etc (for example: clove oil, menthol oil, camphor oil, eucalyptus oil, eugenol, menthyl lactate, witch hazel distillate), anti-acne agents (for example, salicylic acid or benzoyl peroxide), anti-flocculants, anti-foaming agents, antimicrobial agents (for example: iodopropyl butylcarbamate), anti-oxidants (for example, ascorbic acid and its derivatives or tea extracts), anti-wrinkle actives (for example, retinoids or beta-hydroxy acids), binders, biological additives, buffers, swelling agents, chelating agents, additives, biocidal agents, denaturing agents, thickening agents, and vitamins, and their derivatives or equivalents, film-forming materials, polymers, opacifying agents, pH adjusters, reducing agents, de-pigmenting or brightening agents (for example: hydroquinone, kojic acid, ascorbic acid, mulberry extract, magnesium ascorbyl phosphate, ascorbyl glucosamine), conditioning agents (for example: humectants), anti-inflammatory agents (for example, corticosteroids), and sunscreens.

The cosmetic compositions of the present invention may be made into a wide variety of product forms such as are known in the art. These include, but are not limited to, lotions, creams, gels, sticks, sprays, ointments, pastes, mousses, and aerosols.

The cosmetic compositions described herein are particularly useful as part of a method of cosmetic treatment for treating skin having signs of aging or UV damage wherein such compositions are applied to skin in need of such treatment for the duration of time necessary to improve the condition of such skin. Although such duration of time will vary based on the efficacy of such cosmetic composition, it is preferred the cosmetic composition be applied at least once a day to the skin.

EXAMPLES

The present invention is further demonstrated by the way of the following examples, which should not be considered limiting. Unless otherwise stated, the proportions given in any Examples herein are expressed as percentages by weight. The temperature is in degrees Celsius and the pressure is atmospheric pressure.

Example 1

Extracts

Samples of wild-type *Gracilaria* spp. were field collected (obtained in Long Island, N.Y.), rinsed with tap water and allowed to dry at room temperature. Extractions of the algae samples were made as shown below:

| Description | Extraction Method |
|---|---|
| wild-type *Gracilaria* spp. 10% | boiled |
| wild-type *Gracilaria* spp. 10% | water/MeOH reverse extract |
| wild-type *Gracilaria* spp. 10% | H.O. |

The above wild-type extracts were screened for proteasome activity and produced positive results.

Extracts of the species *Gracilaria tikvahiae* were also prepared. *G. tikvahiae* grown by aquaculture were obtained from a commercial supplier in Hawaii, USA. Aqueous extractions were prepared via conventional methodology having a percentage of *Gracilaria* in the extract of 0.5%, 1%, 5%, 10%, 20%, 30%, 40%, 50%, and 60% by weight. The percentage increase of proteasome stimulation of fibroblasts in comparison to a control for all extracts is shown in FIG. 4. The test protocol for proteasome stimulation utilized is described in further detail in Example 3 below.

Example 2

Ferments

Samples of wild-type *Gracilaria* spp. were field collected (obtained in Long Island, N.Y.), rinsed with tap water and allowed to dry at room temperature. The samples of the *Gracilaria* were chopped in a food processor and blended with either *Saccharomyces cerevisae* or *Zygosaccharomyces rouxii*, at the percentage shown below, and an appropriate nutrient broth using a homogenizer. In each case, the mixture was left still and allowed to ferment for 3 days at 30° C., and then filtrated to remove the algae biomass, the yeast, and any other insoluble components from the fermentation broth. The samples are below:
wild-type *Gracilaria* spp./*S. cerevisae* ferment 0.62%
wild-type *Gracilaria* spp./*S. cerevisae* ferment 2.5%
wild-type *Gracilaria* spp./*Z. rouxii* ferment 2.5%

The above wild-type fermentations were screened for proteasome activity and produced positive results.

Raw, fresh, cultivated *G. tikvahiae* was obtained from a commercial supplier (cultivated in Hawaii, USA). The *G. tikvahiae* was chopped in a food processor and blended at 10% w/w with *Z. rouxii*, and a standard nutrient yeast broth (Difco™ Malt Extract Broth, available from Becton-Dixon) using a homogenizer. The aforementioned mixture was left still and allowed to ferment for 3 days at 30° C. The mixture was then filtrated to remove the algae biomass, the yeast, and any other insoluble components from the fermentation broth. The resulting fermentation broth was a pale, translucent liquid.

1% and 2% of the above ferments were tested for proteasome stimulation in fibroblasts. The percent increase of proteasome stimulation over the control is shown in FIGS. 1, 2 and 3.

Example 3

Evaluation of Proteasome Stimulation

Test protocols are described below.
Cell Treatment
Frozen fibroblast cells were thawed into a flask. The media was changed every other day until the cells reached confluency. The cells were trypsinized and plated into 12 well plates. The plates were incubated at 37° C./5% $CO_2$ until about 70% confluency. The cells were then treated with the active components of the present invention at different concentration, and incubated at 37° C./5% $CO_2$ for 3 days. Fibroblasts from "young skin", i.e., neonatal fibroblasts, and "aged skin", aged 57 years fibroblasts and aged 62 years fibroblasts were treated. With 1% and 2% of a *G. tikvahiae/ S. cerevisae* ferment.
Proteasome Assay
Once treatment with the present active components was completed, the cells were washed once with PBS and lysised by lysis buffer on ice for 30 min. The cell lysate was spun down to pellet any cell debris and the supernatant was used for proteasome assay.

50 ul of above cell lysate diluted accordingly and 40 uL of assay buffer and 10 uL of substrate (Suc-LLVY-AMC, AMC(7-Amino-4-methylcoumarin)) was mixed in a assay plate which is good for fluorescence measurement. The plate was incubated for 1.5 hrs at 37° C., and read at 380/460 nm by a fluorometer. Results of the evaluations are shown in FIGS. 6, 7, and 8.

Example 4

Cosmetic Composition

An exemplary cream cosmetic lotion comprising a cosmetic active component of the present invention is as shown in the following table:

| Phase | Vendor | RAW MATERIAL | INCI MOMENCLATURE | % W/W |
|---|---|---|---|---|
| A 010 | Local | Deionized Water | Water | 78.330 |
| A 020 | Local | Disodium EDTA | Disodium EDTA | 0.050 |
| A 030 | Local | Butylene Glycol | Butylene Glycol | 3.000 |
| A 040 | Clariant | Aristoflex AVC/ USA | Ammonium Acryloyldimethyltaurate/ VP Copolymer | 0.700 |
| A 050 | Clariant | Aristoflex HMB | Ammonium Acryloyldimethyltaurate/ Beheneth-25 Methacrylate Crosspolymer | 0.070 |
| B 060 | Seppic | Montanov 68 | Cetearyl Alcohol (and) Cetearyl Glucoside | 3.600 |
| B 070 | Local | Lexol GT-865 | Caprylic/Capric Triglyceride | 5.500 |
| B 080 | Fancor | Fancol Karite Shea Butter | *Butyrospermum Parkii* (Shea Butter) | 1.000 |
| C 090 | Dow Corning | DC1413 | Dimethicone | 2.500 |
| D 100 | BASF | *Gracilaria* algae extract | | 3.000 |
| D 110 | BASF | Germazide PSB | Phenoxyethanol and Chlorphenesin and Benzoic Acid and Butylene Glycol and Sorbic Acid | 1.250 |
| E 120 | Seppic | Simulgel EPG | Sodium Acrylate/Sodium Acryloyldimethyl Taurate Copolymer and Polyisobutene and Caprylyl/Capryl Glucoside | 1.000 |

Example 5

Cosmetic Composition

An exemplary cosmetic cream to powder comprising a marine-derived cosmetic active component of the present invention is as shown in the following table:

| Phase | RAW MATERIAL | INCI NOMENCLATURE | % W/W | EXT. WT |
|---|---|---|---|---|
| A 010 | DI Water | Water | 55.270 | 276.350 |
| A 020 | Disodium EDTA | Disodium EDTA | 0.050 | 0.250 |
| A 030 | Butylene Glycol | Butylene Glycol | 3.000 | 15.000 |
| A 040 | Microma 100 | Polymethyl Methacrylate | 20.000 | 100.000 |
| A 050 | Artistoflex AVC | Ammonium Acryloyldimethyltaurate/VP Copolymer | 0.800 | 4.000 |
| A 060 | Aristoflex HMB | Ammonium Acryloyldimethyltaurate/Beheneth-25 Methacrylate Crosspolymer | 0.080 | 0.400 |
| B 070 | Velvesil DM | Dimethicone, Cetearyl Dimethicone Crosspolymer | 8.000 | 40.000 |
| B 080 | DC 200/200 Fluid | Dimethicone | 8.000 | 40.000 |
| C 090 | Simulgel EPG | Sodium Acrylate/Sodium Acryloyldimethyl Taurate Copolymer and Polyisobutene and Caprylyl/Capryl Glucoside | 0.800 | 4.000 |
| D 100 | Germazide PSB | Phenoxyethanol, Chlorphenesin, Benzoic Acid, Butylene Glycol, Sorbic Acid | 1.000 | 5.000 |
| D 110 | *Gracilaria* algae extract | | 3.000 | 15.000 |

Example 6

Cosmetic Composition

An exemplary anti-aging night cream comprising a marine-derived cosmetic active component of the present invention is as shown in the following table:

| INGREDIENTS | INCI NAME | wt % |
|---|---|---|
| Phase I | | |
| Emulgade ® PL 68/50 | Cetearyl Glucoside (and) Cetearyl Alcohol | 3.0 |
| Cutina ® PES | Pentaerythrityl Distearate | 2.0 |
| Cutina ® CP | Cetyl Palmitate | 0.5 |
| Monomuls ® 90-O 18 | Glyceryl Oleate | 1.0 |
| Cetiol ® Sensoft | Propylheptyl Caprylate | 2.0 |
| Cetiol ® CC | Dicaprylyl Carbonate | 3.0 |
| Myritol ® 331 | Cocoglycerides | 5.0 |
| Cegesoft ® PFO | *Passiflora Incarnata* Seed Oil | 2.0 |
| Coviox ® T70C | Tocopherol | 0.1 |
| Cosmedia ® SP | Sodium Polyacrylate | 0.7 |
| Phase II | | |
| Glycerin | Glycerin | 3.0 |
| Eumulgin ® SG | Sodium Stearoyl Glutamate | 0.5 |
| Elestab ® 388 | Propylene Glycol (and) Phenoxyethanol (and) Chlorphenesin (and) Methylparaben | 1.0 |
| Water | Aqua | q.s. |
| Phase III | | |
| *Gracilaria* extract | | 2.0 |
| Bioplasma | | 1.0 |

Viscosity: Brookfield RVF, 23° C., spd T-E, 5 rpm Helipath: 140,000 cps. pH 5.7

Heat the phase I (with Cosmedia SP) to 80° C.-85° C. and mix homogeneously. Heat phase II to 80° C.-85° C. and add to the oil phase while stirring. Allow the emulsion to cool while stirring in such a way that it remains in continual motion. Avoid incorporation of air. If necessary, homogenize with a suitable dispersion unit (e.g, Ultra Turrax) at approximately 55° C. Add the components of phase III and desired fragrance at 40° C. with moderate mixing. Continue mixing while the batch is cooling to 30° C.

Example 7

Cosmetic Composition

An exemplary body butter comprising a marine-derived cosmetic active component of the present invention is as shown in the following table:

| INGREDIENTS | INCI NAME | wt % |
|---|---|---|
| Phase I | | |
| Emulgade ® Sucro | Sucrose Polystearate (and) Hydrogenated Polyisobutene | 4.0 |
| Eumulgin ® SG | Sodium Stearoyl Glutamate | 0.5 |
| Cutina ® PES | Pentaerythrityl Distearate | 3.0 |
| Cutina ® GMS-V NA | Glyceryl Stearate | 1.0 |
| Cetiol ® Sensoft | Propylheptyl Caprylate | 5.0 |
| Cetiol ® SB45 | *Butyrospermum Parkii* (Shea Butter) | 9.5 |
| Cegesoft ® GPO | Palm (*Elaeis Guineensis*) Oil | 1.0 |
| Cegesoft ® SH | *Shorea Stenoptera* Seed Butter | 2.0 |
| DC 200 Fluid 350 CST | Dimethicone | 1.0 |
| Phase II | | |
| Glycerin | Glycerin | 3.0 |
| Elestab ® PB Free LS 9842 | Water (and) Phenoxyethanol (and) Glycerin (and) Sorbic Acid | 2.0 |
| Water | Aqua | q.s. |
| Phase III | | |
| Cosmedia ® SP | Sodium Polyacrylate | 1.0 |
| Phase IV | | |
| *Gacilaria* extract | | 2.0 |
| Oleuropein | | 1.0 |

Viscosity: Brookfield RVF, 23 C., spd T-E, 5 rpm, Helipath: 320,000
pH: 6.0

Heat the oil phase I to 80° C.-85° C. and mix homogeneously. Heat phase II to 80° C.-85° C. and add to the oil phase with moderate mixing. Allow the emulsion to cool while stirring in such a way that it remains in continual motion. Homogenize, and then add phase III with vigorous mixing. Continue cool down to ambient temperature with moderate mixing. Avoid the incorporation of air. Add phase IV and desired fragrance at 40° C. with moderate mixing. Continue mixing while the batch is cooling to 30° C.

Example 8

Cosmetic Composition

An exemplary eye cream comprising a marine-derived cosmetic active component of the present invention is as shown in the following table:

| INGREDIENTS | INCI NAME | wt % |
|---|---|---|
| Phase I | | |
| Dehymuls ® PGPH | Polyglyceryl-2 Dipolyhydroxystearate | 4.0 |
| Lanette ® 22 | Behenyl Alcohol | 2.0 |
| Cetiol ® Sensoft | Propylheptyl Caprylate | 3.0 |
| Myritol ® 331 | Cocoglycerides | 5.0 |
| Cetiol ® J600 | Oleyl Erucate | 5.0 |
| Cegesoft ® VP | Vegetable Oil (and) Hydrogenated Vegetable Oil (and) *Euphorbia Cerifera* (Candelilla) Wax | 5.0 |

-continued

| INGREDIENTS | INCI NAME | wt % |
|---|---|---|
| DC 200 Fluid 350 CST | Dimethicone | 0.5 |
| Phase II | | |
| Water | Aqua | q.s. |
| Elestab ® 388 | Propylene Glycol (and) Phenoxyethanol (and) Chlorphenesin (and) Methylparaben | 1.0 |
| Glycerin | Glycerin | 3.0 |
| Cosmedia ® SP | Sodium Polyacrylate | 0.8 |
| Phase III | | |
| Plantapon ® LGC Sorb | Sodium Lauryl Glucose Carboxylate (and) Lauryl Glucoside | 1.5 |
| Phase IV | | |
| *Gracilaria* extract | | 2.0 |
| Prolixir S20 | | 1.0 |
| Fragrance | | q.s |

Viscosity: Brookfield RVT, 23 C., spindle T-E, 5 rpm, with Helipath: 70,000 cps
pH: 5.8

Slowly add Cosmedia SP into phase II while heating to 75~80° C. with a vigorous agitation until a homogenous gel forms. Add phase III into phase II with moderate mixing (avoid incorporating air). Pre-heat phase I to 75~80° C. then add into phase II+III with moderate mixing. When the batch becomes homogenous, start to cool down with moderate mixing. Homogenize the batch at 55~60° C. Continue moderate mixing while the batch cools down. Add ingredients in phase IV one at a time with moderate mixing below 50° C. Add desired fragrance with moderate mixing when temperature is below 40° C.

Example 9

Cosmetic Composition

An exemplary long lasting moisturizing lotion comprising a marine-derived cosmetic active component of the present invention is shown in the following table:

| INGREDIENTS | INCI NAME | wt % |
|---|---|---|
| Phase I | | |
| Lanette ® E | Sodium Cetearyl Sulfate | 0.25 |
| Lanette ® O | Cetearyl Alcohol | 1.0 |
| Cutina ® GMS-V | Glyceryl Stearate | 2.0 |
| Fitoderm | Squalane | 2.0 |
| Cetiol ® SB45 | Shea Butter | 1.0 |
| Cetiol ® EHP | Ethylhexyl Palmitate | 4.0 |
| Myritol ® 312 | Caprylic/Capric Triglyceride | 3.0 |
| Generol ® 122N PRL | *Glycine Soja* (Soybean) Sterols | 1.0 |
| DC 200 Fluid 350 CST | Dimethicone | 0.5 |
| Phase II | | |
| Cosmedia ® SP | Sodium Polyacrylate | 0.3 |
| Phase III | | |
| Water | Aqua | q.s. |
| Glycerin | Glycerin | 3.0 |
| Preservative | Preservative | q.s. |
| *Gracilaria* extract | | 2.0 |
| Delentigo | | 1.0 |

Viscosity: Brookfield RVT, 23° C. (spindle # T-E @ 5 rpm): 90,000 cps
pH: 6.2

Heat the phase I to 80-85° C. and mix homogeneously. Sprinkle Cosmedia SP into phase I with moderate mixing until homogenously. Pre-heat phase III to 80-85° C. and add into phase I+II. Homogenize the batch at 55° C. Continue cool down to ambient temperature with moderate mixing. Avoid the incorporation of air. Add desired fragrance with moderate mixing when temperature is below 40° C.

Example 10

Cosmetic Composition

An exemplary PIT spray comprising a marine-derived cosmetic active component of the present invention is as shown in the following table:

| INGREDIENTS | INCI NAME | wt % |
|---|---|---|
| Phase I | | |
| Emulgade ® SE-PF | Glyceryl Stearate (and) Ceteareth-20 (and) Ceteareth-12 (and) Cetearyl Alcohol (and) Cetyl Palmitate | 3.9 |
| Eumulgin ® B 2 | Ceteareth-20 | 1.1 |
| Cetiol ® Sensoft | Propylheptyl Caprylate | 5.0 |
| Cetiol ® CC | Dicaprylyl Carbonate | 2.0 |
| Cegesoft ® SB | Shea Butter | 0.5 |
| Coviox ® T70C | Tocopherol | 0.5 |
| Phase II | | |
| Spa Day (Symrise) | Fragrance | 0.3 |
| Phase III | | |
| Water | Aqua | q.s. |
| Glycerin | Glycerin | 2.0 |
| Elestab ® 388 | Propylene Glycol (and) Phenoxyethanol (and) Chlorphenesin (and) Methylparaben | 1.0 |
| Phase IV | | |
| Water (Cold) | Aqua | 20.0 |
| Phase V | | |
| *Gracilaria* extract | | 2.0 |
| *Phaeodactylum* algae extract | | 1.0 |

Viscosity: Brookfield RVT, 23 C., <400 cps spindle #5, 10 rpm:
pH 5.0

Heat phase I to 90-95° C. and stir until homogeneous. Keeping the temperature constant at 90-95° C., add phase II into phase I right before adding phase III to avoid overheating the fragrance. Pre-heat phase III to 90-95° C. and pour into phase I+II. Cool the batch as fast as possible while mixing. At 55-60° C., add phase IV with moderate mixing. Keep cooling the emulsion to ambient temperature with slow mixing. Add phase V while the batch is below 40° C.

Example 11

Cosmetic Composition

An exemplary natural or "green" body lotion comprising a marine-derived cosmetic active component of the present invention is shown in the following table:

| INGREDIENTS | INCI NAME | wt % |
|---|---|---|
| Phase I | | |
| Emulgade ® PL 68/50 | Cetearyl Glucoside (and) Cetearyl Alcohol | 4.0 |
| Cutina ® CP | Cetyl Palmitate | 2.0 |
| Monomuls ® 90-O 18 | Glyceryl Oleate | 0.5 |
| Cetiol ® OE | Dicaprylyl Ether | 5.0 |

-continued

| INGREDIENTS | INCI NAME | wt % |
| --- | --- | --- |
| Cegesoft ® VP | Vegetable Oil (and) Hydrogenated Vegetable Oil (and) *Euphorbia Cerfera* (Candelilla) Wax | 5.0 |
| Cetiol ® SB45 | *Butyrospermum Parkii* (Shea Butter) | 1.0 |
| Phase II | | |
| Glycerin | Glycerin | 3.0 |
| Eumulgin ® SG | Sodium Stearoyl Glutamate | 1.0 |
| Water | Aqua | q.s |
| Keltrol CG T (CP Kelco) | Xanthan Gum | 0.5 |
| Veegum Pure (RT Vanderbilt) | Magnesium Aluminum Silicate | 2.0 |
| Potassium Sorbate | Potassium Sorbate | 0.3 |
| Benzyl Alcohol | Benzyl Alcohol | 2.0 |
| Phase III | | |
| *Gracilaria* extract | | 2.0 |
| *Cochleria* extract | | 1.0 |
| Citric Acid pH < 7.0 | Citric Acid | q.s. |

Viscosity: Brookfield RVT, 23 C., spindle T-E, 5 rpm: 48,000 cps
pH: 6.50

Combine all ingredients in phase II, while heating to 80-85° C., mixing with a vigorous mix until Veegum Pure and xanthan gum are properly hydrated. Add phase I to phase II with a strong mixing. When the batch becomes homogenous, start to cool down with moderate mixing. Homogenize the batch at 55-60° C. When temperature drop below 40° C., add phase III and adjust pH with Citric Acid to desire pH. Add desired fragrance with moderate mixing when temperature is below 40° C.

What is claimed is:

1. A topical composition for increasing proteasome activity in fibroblasts of human skin comprising an effective amount of a fermentation broth obtained by inoculating a biomass of algae of the species *Gracilaria* and a live yeast culture within a broth and fermenting the broth for a suitable time, wherein the effective amount of said fermentation broth is in the range of about 0.1% to 5% by weight based on the final weight of the composition.

2. The topical composition of claim 1 wherein the topical composition comprises between about 0.01% and about 10% by weight of the cosemetic active component.

3. The topical composition of claim 1, wherein the yeast is *Saccharomyces cerevisae*.

4. The topical composition of claim 1, wherein the yeast is *Zygosaccharomyces rouxii*.

5. The topical composition of claim 1, comprising an additional cosmetic active component wherein the second cosmetic active component is derived from a marine plant or animal.

6. The topical composition of claim 1, wherein the *Gracilaria* species is *Gracilaria tikvahiae*.

7. The topical composition of claim 1, wherein the *Gracilaria* species is *Gracilaria gracilis*.

8. The topical composition of claim 1, wherein the *Gracilaria* species is *Gracilaria parvispora*.

9. The topical composition of claim 1, wherein the *Gracilaria* species is *Gracilaria vermiculophylia*.

10. The topical composition of claim 1, wherein the composition further comprises at least one ingredient selected from the group consisting of preservatives, emollients, emulsifying agents, surfactants, moisturizers, gelling agents, thickening agents, conditioning agents, film-forming agents, stabilizing agents, anti-oxidants, texturizing agents, gloss agents, mattifying agents, solubilizers, pigments, dyes, and fragrances.

11. The topical composition of claim 1, further comprising an additional cosmetic active component which increases, stimulates and/or modulates proteasome activity in the skin.

12. The topical composition of claim 11, wherein the additional cosmetic active component is derived from a marine plant.

13. The topical composition of claim 11, wherein the topical composition comprises between about 1% and about 5% by weight of the fermentation broth based on the final weight of the composition and the yeast is *Saccharomyces cerevisa* or *Zygosaccharomyces rouxii*.

14. The topical composition of claim 13, wherein the additional cosmetic active component is derived from a marine plant.

15. The topical composition of claim 1, wherein the topical composition comprises between about 1% and 3% by weight of the fermentation broth based on the final weight of the composition.

16. The topical composition of claim 15, wherein the yeast is *Saccharomyces cerevisa*.

17. The topical composition of claim 15, wherein the yeast is *Zygosaccharomyces rouxii*.

* * * * *